(12) United States Patent
Patrice

(10) Patent No.: US 8,143,017 B2
(45) Date of Patent: Mar. 27, 2012

(54) METHOD OF MEASURING THE ABILITY OF A SAMPLE TO WITHSTAND REACTIVE OXYGEN SPECIES (ROSS)

(76) Inventor: Thierry Patrice, Saint Herblain (FR)

( * ) Notice: Subject to any disclaimer, the term of this patent is extended or adjusted under 35 U.S.C. 154(b) by 0 days.

(21) Appl. No.: 12/741,455

(22) PCT Filed: Nov. 13, 2008

(86) PCT No.: PCT/FR2008/052042
§ 371 (c)(1),
(2), (4) Date: Jun. 11, 2010

(87) PCT Pub. No.: WO2009/068820
PCT Pub. Date: Jun. 4, 2009

(65) Prior Publication Data
US 2010/0267077 A1 Oct. 21, 2010

(30) Foreign Application Priority Data

Nov. 13, 2007 (FR) ..................................... 07 07938
Apr. 16, 2008 (FR) ..................................... 08 02110

(51) Int. Cl.
*C12Q 1/02* (2006.01)
*C12P 21/06* (2006.01)
*C07K 1/00* (2006.01)

(52) U.S. Cl. .......................... 435/29; 435/69.1; 530/350

(58) Field of Classification Search ................. 435/29, 435/69.1; 530/350
See application file for complete search history.

(56) References Cited

FOREIGN PATENT DOCUMENTS

| EP | 0 563 114 | 11/1997 |
| WO | 92/10759 | 6/1992 |
| WO | 03/016527 | 2/2003 |
| WO | 2004/034058 | 4/2004 |

OTHER PUBLICATIONS

Chingell et al. A Photochemical Study of Cells Loaded with of 2′,7-Dichlorofluorescin: Implications for the Detection of Reactive Oxygen Species Generated During UVA Irradiation. 2002. Free Radical Biology and medicine 34(8) 1029-1034.*

P. Bilski et al., "Photosensitized oxidation of 2′, 7′ -dichlorofluorescin: singlet oxygen does not contribute to the formation of fluorescent oxidation product 2′, 7 -dichlorofluorescein", Free Radical Biology & Medicine 1 Oct. 1, 2002, vol. 33, No. 7, pp. 938-946, XP-002500240, ISSN: 0891-5849.

F. Vargas et al., "Antioxidant and Scavenging Activity of Emodin, Aloe-Emodin, and Rhein on Free-Radical and Reactive Oxygen Species", Pharmaceutical Biology, vol. 42, No. 4-5, Jun. 2004, pp. 342-348, XP009107274.

International Search Report dated Jun. 9, 2009, from corresponding PCT application.

\* cited by examiner

*Primary Examiner* — Karen Carlson
*Assistant Examiner* — Natalie Moss
(74) *Attorney, Agent, or Firm* — Young & Thompson

(57) ABSTRACT

A method of measuring the ability of a biological sample to withstand reactive oxygen species (ROSs). The method includes at least the steps of putting the sample for testing and a photosensitive agent in a liquid medium into contact so as to form a mixture for testing, subjecting the mixture for testing to a dose of light irradiation so as to give rise, by photochemical reaction, to the production of reactive oxygen species, then after irradiation, adding a compound that reacts colorimetrically in the presence of reactive oxygen species (ROSs) to form a chromogen or fluorescent substance, and measuring the quantity of chromogen or fluorescent substance that is produced, and also subjecting a reference mixture to the same photochemical, colorimetric, and measurement reactions as the mixture for testing.

10 Claims, 4 Drawing Sheets

METHOD OF MEASURING THE ABILITY OF A SAMPLE TO WITHSTAND REACTIVE OXYGEN SPECIES (ROSS)

The present invention relates to a method of measuring the total antioxidant status (TAS) of a biological sample from a human or animal organism, i.e. its ability to withstand reactive oxygen species (ROSs), and it also relates to a test kit suitable in particular for enabling said method to be implemented.

More particularly, the invention relates to a method using a photochemical reaction for measuring the ability of a biological liquid, a tissue, or a tissue extract, and more generally a material from a living or dead human or animal organism to withstand oxidative stress and reactive oxygen species (ROSs) produced during normal or pathological metabolism or induced when implementing treatment.

Oxidative stress has been the subject of numerous studies over the last few years because it is involved in a large number of normal, pathological, or therapeutic processes. Tests for quantifying such and such a factor involved in defense against ROSs have been devised. Systems enabling total antioxidant status (TAS) to be measured have also been developed: Imanox TAS kit, Randox kit (EP-0 563 114), WO 03/016527. The invention lies in the context of measuring TAS. Furthermore, potential sources of ROSs have been identified, and amongst them it has been shown that photochemical reactions produce ROSs of natures and in quantities that vary as a function of the chemical nature of the photosensitizer, of the intensity of the light delivered to the photosensitizer, and of the nature of the tissue that has been sensitized by the photosensitizer prior to light irradiation. In this context, the most reactive primary ROS that is formed in the largest quantities is singlet oxygen ($^1O_2$).

Oxidative stress and ROSs are produced when materials are exposed to chemical or physical agents, e.g. plastics materials exposed to the sun, or in biology in physiological phagocytosis reactions by white corpuscles leading to the destruction of bacteria, for example, but also and above all during numerous biochemical reactions of normal or pathological metabolism. ROSs produced in excess or that are insufficiently neutralized will have deleterious effects that may lead to accelerated aging of biological or other constituents, to early degradation of biological tissues, or even of materials. Amongst pathologies that are directly or indirectly linked with ROSs, mention may be made of Alzheimer's disease, diabetes and its consequences, certain cancers, certain degenerative pathologies of bone tissue and cartilage, and atherosclerosis. More generally, one hypothesis concerning the aging of living beings also relies on deleterious oxidizing action of ROSs spoiling in diffuse manner all protein, lipid, and/or glutide biological constituents.

Amongst reactive oxygen species, mention may be made of the superoxide radical $O_2^-$, the perhydroxyl radical HOO., the hydroxyl radical HO., the peroxyl radical ROO., the alkoxyl radical RO., and the nitroxyl radical NO.. All these ROSs are free radicals, i.e. chemical species possessing a lone electron in their peripheral layers. These free radicals that intervene have a lone electron on an oxygen atom. Singlet oxygen, $^1O_2$, is one of two excited forms of oxygen. Singlet oxygen is not a radical and does not have a lone electron.

The lifetime of singlet oxygen is a few microseconds in an aqueous medium.

Singlet oxygen is produced either by a discharge between electrodes, or chemically, or by a photochemical reaction, with rose bengal having very high quantum efficiency of about 0.75 in producing $^1O_2$. Singlet oxygen reacts with various substrates to form reactive oxygen species (primary ROSs) that themselves become progressively deactivated by forming secondary ROSs of lower oxidizing potential, and so on as a function of time.

Free radicals spoil various biological targets and in particular lipids, proteins, and nucleic acids. These radical species are involved in numerous pathologies that are grouped together under the term oxidative stress. The factors that increase the action of ROSs are numerous, and one of major importance is the partial pressure of oxygen in tissue, and thus its pH, and from a biological point of view all of the enzymes that regulate cell death. The factors that decrease the action of ROSs are also numerous: proteins, vitamins, superoxide dismutase (SOD), the glutathione and glutathione peroxidase system, etc. The action of a ROS is a kind of comprise between its reactivity, its lifetime, and its affinity relative to such and such a biological constituent or target. Antioxidant substances present very high affinity for ROSs, thereby deflecting them from some other constituent that would otherwise have been attacked thereby. In spite of that, any compound that is subjected to a ROS attack and that possibly includes an antioxidant substance will in turn become oxidizing and potentially deleterious, albeit with reactivity that is less than that of the ROS. Any added reagent, including a reagent added for detection, and a fortiori for causing or inhibiting the oxidizing reaction, may also under certain circumstances behave in the same manner in the presence of ROSs. Thus, detoxifying ROSs is a kind of cascade of events leading to ROSs being neutralized progressively as a function of time.

In order to study ROSs, it is possible to analyze their production by detecting them either directly, however that is not possible for most species, and in particular that is difficult for $^1O_2$ (the measured lifetime of $^1O_2$ luminescence at 1270 nanometers (nm) in water is 5 microseconds (µs)), or indirectly, and for most of them that is impossible to set up simply in a given material or tissue, in particular for ground tissues or biological liquids because reactivity decreases rapidly and because it is impossible to perform real time measurement over a long duration. It is possible to analyze the transformation of a colored or fluorescent marker under the influence of ROSs being produced or circulating. However the reaction that leads to the production of ROSs also often leads to the destruction of the marker. In a commercially-available test, an oxidizing chemical substance is caused to react with the substrate for which it is desired to measure ability to withstand ROS (TAS). However, in that test, the reagent, which remains in solution, forms part of the measurement since the substance is not neutralized and is therefore a source of artifacts. This applies for example to the article by Franklin R. Vargas et al. "Antioxidant and scavenging activity of emodin, aloe-emodin, and rhein on free radical and reactive oxygen species", Pharmaceutical Biology, Vol. 42, No. 4-5, June 2004 (2004-06), pp. 342-348. That document describes a method of determining the antioxidant status of several organic compounds. The method is based on a reaction of oxygen in the form of $^1O_2$ with the compounds mentioned, and on detecting the concentration of $^1O_2$ by fluorescence during the reaction. In its implementation, the photochemical reaction that generates the production of singlet oxygen operates in the presence of the developer, i.e. a colorimetric compound, specifically luminol. Subjecting luminol to light irradiation generates artifacts. As a result, in that document, the luminol directly detects the singlet oxygen produced by photochemical reaction.

The document by P. Bilski et al. "Photosensitized oxidation of 2',7'-dichlorofluoresceine: single oxygen does not contribute to the formation of fluorescent oxidation product 2',7'-dichlorofluoresceine", Free Radical Biology & Medicine, Oct. 1, 2002, Vol. 33, No. 7, Oct. 1, 2002 (2002-10-01), pp. 936-946 mentions in its title that single oxygen does not contribute to forming fluorescent dichlorofluoresceine. Once more, in his experiments with a biological sample, Bilski proceeds in a manner analogous to Vargas, i.e. he irradiates the colorimetric component, assuming that any other action, in particular with an agent such as dichlorofluoresceine, would lead to results that are erroneous or not interpretable.

Document WO 92/10759 does not describe any photochemical reaction. The same applies to document WO 2004/034058.

Furthermore, previously made applications make no mention of overall measurements performed at tissue level. Finally, it is possible to study individual factors that influence the reactivity of ROSs, either by assaying them or by measuring how they are transformed under the influence of ROSs, but that is time-consuming, expensive, and does not take account of interactions between quenchers.

It is to mitigate those difficulties and to satisfy the need to be able to perform an overall measurement of the ability to withstand ROSs, also known as TAS, and corresponding to measuring the ability to inhibit ROSs, that the method of the present invention has been developed.

An object of the present invention is thus to propose a measurement method that, on being implemented, serves to reduce or eliminate sources of artifacts, and to obtain a measurement that is reliable and reproducible.

To this end, the invention provides a method of measuring the total antioxidant status (TAS) of a biological sample from a human or animal organism, i.e. its ability to withstand reactive oxygen species (ROSs), said method being characterized in that it comprises at least the following steps:

putting the biological sample for testing into contact with a photosensitive agent in a liquid medium to form a mixture for testing;

subjecting said mixture for testing to a dose of light irradiation at a wavelength that is absorbed by the photosensitive agent in order to give rise, by a photochemical reaction at least between the light and the photosensitive agent, to at least the production of singlet oxygen suitable for co-operating with said sample to form reactive oxygen species (ROSs);

adding, after irradiation, a compound that reacts colorimetrically in the presence of reactive oxygen species (ROSs) to form a chromogen or fluorescent substance;

measuring the quantity of chromogen or fluorescent substance produced over time in order to determine the ability of said sample to withstand reactive oxygen species (ROSs) by inhibiting them, a low level of chromogen or fluorescent substance production corresponding to said sample having a high ability to withstand reactive oxygen species (ROSs);

subjecting at least one reference mixture formed by mixing a reference biological sample from a presumed healthy organism with a photosensitive agent to the same photochemical, colorimetric, and measurement reactions as the mixture for testing; and comparing the measurement results on the mixture for testing with the measurement results obtained on said at least one reference mixture.

The quantity of chromogen or fluorescent substance produced is measured as a function of time.

By adding the compound that is suitable for forming a chromogen or fluorescent substance to the ROS solely after the light irradiation, the compound is not itself degraded by said irradiation. In addition, it is not the reaction of the chromogen or fluorescent substance with the singlet oxygen that is measured, but rather its reaction with reactive oxygen species themselves derived from the reaction of the singlet oxygen with the biological sample for testing. Thus, the ephemeral nature of single oxygen becomes an advantage.

It should be observed that it is also possible to use the mixture of sample for testing and photosensitive agent and the mixture of reference sample and photosensitive agent as controls for the purpose of correcting the data obtained by photochemical and colorimetric reactions by subjecting said controls solely to a colorimetric reaction.

When implementing a method of the type in which the mixture of the sample for testing with a photosensitive agent and the mixture of a reference sample with a photosensitive agent are subjected to the same photochemical, colorimetric, and measurement reactions, the method comprises, during the measurement step, measuring over time, for each mixture, the quantity of chromogen or fluorescent substance produced in the form of the intensity of the light or fluorescent signal from said substance, said measurement step being followed by a step of processing said measurements, during which, for each mixture, the curve is established for the intensity of the light signal from the chromogen substance as a function of time, and then the area under the curve is calculated, and the ratio is determined between the areas of the mixture for testing and of the reference mixture.

As mentioned above, the results obtained from the colorimetric reaction on its own, without subjecting the mixture for testing and the reference mixture to photochemical reaction, may be subtracted from the curves obtained after the photochemical and colorimetric reactions.

Preferably, a photosensitive agent is used that produces a majority of singlet oxygen $^1O_2$, said agent preferably being selected from the group formed by rose bengal and tetra (4 sulfonato-phenyl)porphyrin (TPPS).

Also preferably, a photosensitive agent is selected that, in the absence of light, does not react with the biological sample for testing, and said photosensitive agent is irradiated at a selected wavelength corresponding to the spectrum absorption maximum of the photosensitive agent.

Generally, prior to putting the sample for testing and the reference sample into contact with the photosensitive agent for light irradiation, the absorbances of the sample for testing and of the reference sample are measured.

An important point is to measure the final absorbance of the solution in which it is desired to measure TAS, and to do so before giving rise to the photochemical reaction by light irradiation. The light that is used for exciting the sensitive agent that causes the photochemical reaction enabling TAS to be measured will be influenced by said absorbance, and consequently the intensity of the photochemical reaction used for measuring TAS will be modified, and in particular will be reduced if the absorbance is too great. Similarly, the measurement of the fluorescence emitted after the photochemical reaction will be influenced by the absorbance of the solution. The measurement of the area under the curve must therefore be calculated as a function of the absorbance and this must be done for all absorbance values that give rise to linear variations in the areas under the curve, which implies that calibration is necessary.

In other words, an absorbance value of the sample for testing, representative of a sample that is cloudy or too colored, serves to exclude said sample from the remainder of the analysis since it is clear that such a sample will give rise to problems, in particular because it does not allow light to pass well during the photochemical reaction and therefore gives rise to an erroneous optical measurement during the colorimetric reaction.

Preferably, the compound that reacts to form a chromogen substance is the reduced dichlorofluoresceine-dichlorofluoresceine system (DCFH-DCF).

Generally, the photochemical and colorimetric reactions are performed at a pH that is neutral or close to biological pH in a thermostated enclosure.

Preferably, the biological sample for testing from a human or animal organism is a biological fluid such as serum, plasma, or a tissue extract in solution. The reference biological sample is of the same nature as the biological sample for testing and comes from a carrier organism that is presumed healthy. Preferably, for each mixture, the quantity of chromogen or fluorescent substance produced is measured in the form of the intensity of the light or fluorescent signal from said sample over a period of time of not less than 45 minutes (min), preferably lying in the range 50 min to 90 min.

The invention also provides a test kit for measuring the total antioxidant status (TAS) of a biological sample from a human or animal organism, i.e. its ability to withstand reactive oxygen species (ROSs), the kit being characterized in that it comprises at least one photosensitive agent suitable for producing by photochemical reaction at least singlet oxygen suitable for co-operating with said sample to form reactive oxygen species, an agent suitable for forming a chromogen or fluorescent substance in the presence of reactive oxygen species, and instructions for using them in accordance with the above-specified method.

The invention also provides a test kit characterized in that it includes at least firstly a support defining at least two compartments, and secondly a photosensitive agent and an agent suitable for forming a chromogen or fluorescent substance, each disposed in a buffered medium in a respective one of the compartments of the support, said compartments being suitable for being put into communication with each other.

The invention can be better understood on reading the following description of embodiments, with reference to the accompanying drawings, in which.

Figure 6:
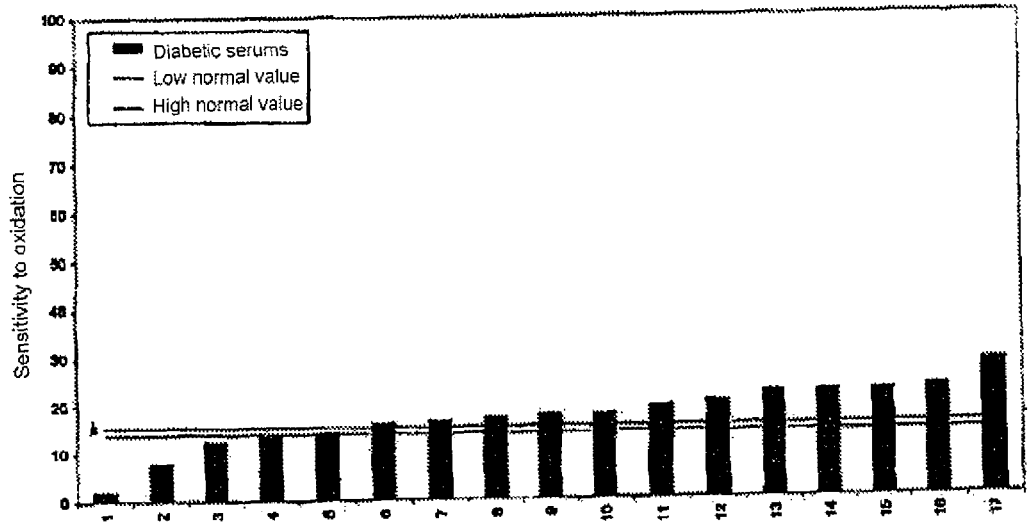
Figure 7:
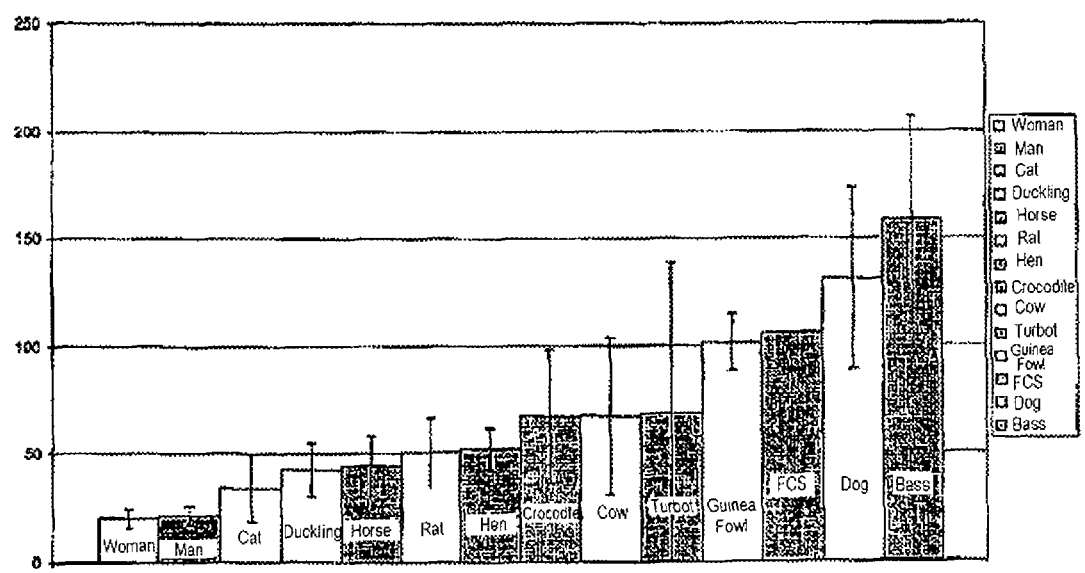

FIG. 6 shows the area under the curve of the dichlorofluoresceine (DCF) fluorescence signal for 17 samples of serum taken from diabetic patients and subjected to light irradiation in the presence of rose bengal, compared with serums from reference healthy humans; and FIG. 7 shows the area under the curve of the dichlorofluoresceine (DCF) fluorescence signal for serum taken from animals of different species (minimum number of individuals per species=8) and subjected to light irradiation in the presence of rose bengal.

As mentioned above, the method of the invention, which consists in measuring the ability of a biological sample to withstand reactive oxygen species (ROSs), comprises at least the following successive steps:

a) a step of putting the sample for testing into contact with a photosensitive agent in a liquid medium so as to form a mixture for testing;

b) a step of subjecting said mixture for testing to a dose of light irradiation in order to give rise at least to the production of singlet oxygen suitable for forming reactive oxygen species with said sample;

c) a step, after irradiation, of adding to said irradiated mixture a compound that reacts colorimetrically in the presence of reactive oxygen species (ROSs) to form a chromogen or fluorescent substance; and d) a step of measuring the quantity of the chromogen or fluorescent substance produced in order to determine the ability of said sample to withstand oxygen reactive species (ROSS).

The method also comprises subjecting a reference biological sample from a presumed healthy carrier to above-described steps a), b), c), and d). The steps a) to d) of the method may be implemented on samples for testing and on reference samples equally well in series or in parallel.

The steps of photochemical and colorimetric reactions and the measurement step are followed by a step of comparing the results. To form this comparison step, a curve is established for each mixture giving the intensity of the light signal of the chromogen substance as a function of time, and then the area under the curve is calculated and the ratio is determined between the areas of the mixture for testing and of the reference mixture.

An implementation of the method may thus consist in adding to the photosensitive reagent: rose bengal present at a concentration of 5 micrograms per milliliter ($\mu m/mL$); and a solution for testing (e.g. serum, FCS, or any other substrate consisting of a biological material, biological tissue, or biological liquid, possibly containing substances that for which it is desired to measure the antioxidant potential and for which it is desired to measure the antioxidant status as a function of time). The volume of the solutions of sample for testing preferably lies in the range 1 microliter ($\mu L$) to 50 $\mu L$. All of the substances are in solution in water and buffered to a pH of 7.2 by adding concentrated phosphate buffer (250 millimoles (mM)). By way of example, the irradiation is performed with a laser emitting with fluence of 1 $J/cm^2$ to 10 $J/cm^2$ at 514 nanometers (nm) (for 10 seconds (s) to 50 s of irradiation). The developer, reduced dichlorofluoresceine (DCFH) (or reduced DCF) is added by an automatic device at the end of light irradiation and stirred. The concentration of the compound lies in the range 0.01 $\mu g/mL$ to 1 mg/mL. The DCFH is thus added after the singlet oxygen has disappeared and the oxygen reactive species has begun to be produced. In general, the chromogen substance is added immediately after the end of light irradiation. These two operations are thus substantially synchronous.

The fluorescence is analyzed in a system that is also thermostated for all of the solutions. Measurements are taken at identical intervals for all of the solutions. At the end of a period lying in the range 10 min to 60 min, the areas under the curve are calculated, as are the slopes serving to characterize the curves showing variation in the fluorescence at different times, e.g. at 1, 2, 5, 10, 20, 40, and 60 minutes. These manipulations make it possible to obtain ratios of areas under the curve that vary as a function of the concentration of the test serum, extract, etc. Thus, when the substance for testing presents a deficit in antioxidant power, there is an increase in the ratios of area under the curve, and when there is hyperantioxidant protection or activity, there is a reduction in said ratios compared with the controls. Normality is assessed relative to normal serums or normal extracts for reference taken from healthy carriers.

As mentioned above, the first step of the method serves to perform a photochemical reaction under thoroughly standardized conditions in order to produce singlet oxygen ($^1O_2$) in particular by means of a photosensitive agent. A photosensitive agent producing singlet oxygen is placed in solution, e.g. in water. Preferably, the concentration of the photosensitive agent lies in the range 0.01 am/mL to 1 mg/mL. A sample is added to said solution, e.g. a serum, a ground biological tissue, or a biological liquid, possibly containing substances for which it is desired to measure the antioxidant potential (e.g. amiothiols, vitamin C or E, etc. . . . ), and for which it is desired to measure the antioxidant status on which primary and secondary ROSs will react after light irradiation at a wavelength that is absorbed by the photosensitive agent. The mixture is buffered by adding phosphate buffer (250 mM) at pH 7.2, and thermostated. Light irradiation is performed at a wavelength that is absorbed by the photosensitive agent. The energy delivered is such that it does not lead to a rise in temperature in the irradiated mixture, which is thermostated. This light irradiation is obtained from a laser or any other type of light source enabling irradiation to be performed at appropriate wavelength and intensity. Synchronously, at the end of irradiating the mixture containing the photosensitive agent and the sample, a known or unknown developer is added, e.g. the reduced dichlorofluoresceine and dichlorofluoresceine (DCFH-DCF) system that generates fluorescence after attack by residual ROSs, as the reactivity of the ROSs produced by the initial photochemical reaction is deactivated in cascade. Thereafter, the oxidizing activity of the residual ROSs is measured as a function of time and in thermostated manner by means of said fluorescence.

Figure 3:
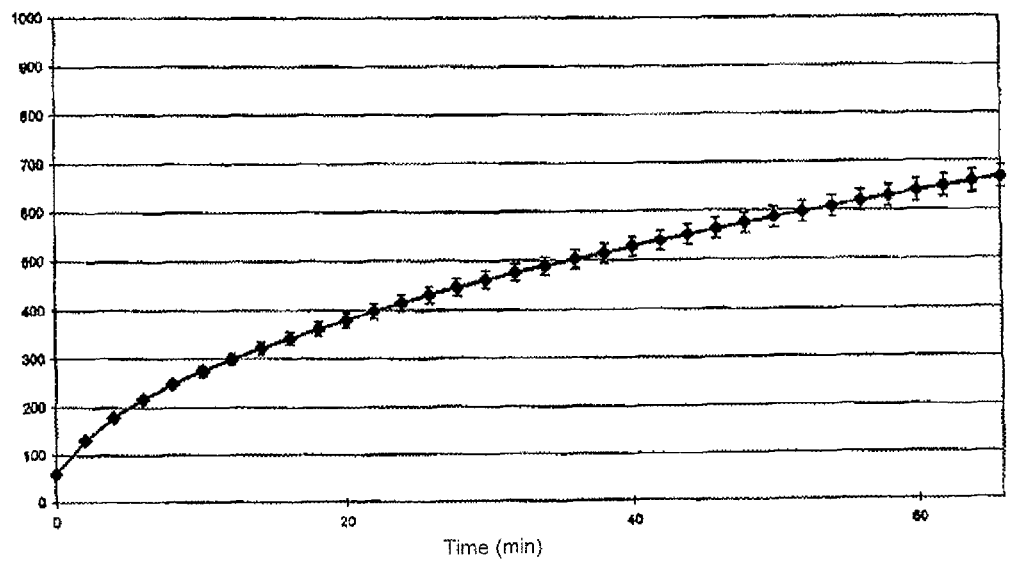
FIG. 3 shows the mean variation of the fluorescence of the dichlorofluoresceine (DCF) signal expressed in arbitrary units as a function of time for 40 analyses of the same sample of fetal calf serum (FCS), and it shows the reproducibility of the method of the present invention.

The disappearance of ROSs observed by measuring their presence as revealed by DCFH-DCF represents the total ability as a function of time of a material, a biological tissue or a biological liquid, to inhibit ROSs and thus to limit the deleterious effects thereof within the sample for which it is desired to measure the TAS. The form of the signal obtained by a suitable colored or fluorescent reagent, an example may be fluorescent DCF after DCFH has been attacked by ROSs, is characteristic of the material subjected to the photochemical reaction and completely different from the signal that is obtained in the absence of the biological material or liquid. Furthermore, fluorescence varies in completely reproducible manner from one experiment to another when the light irradiation for an identical sensitizing agent is performed 40 times in succession in the presence of an identical substrate (fetal calf serum (FCS)) (FIG. 3).

It is thus indeed the variation as a function of time in the resulting signal that is analyzed and that corresponds to the progressive deactivation of the ROSs that are produced, leading to a transformation of DCFH into DCF of fluorescence that increases with increasing numbers of ROSs that have interacted with the non-fluorescent form of DCFH-DCF, written DCFH. This is not any kind of artifact, even if it is not possible to exclude some contribution of self-oxidation of DCFH into DCF at this stage. However even under such circumstances, that contribution is itself proportional to the intensity with which ROSs are produced by the photochemical reaction and inversely proportional to the TAS of the medium being subjected to measurement. At the end of measurement, the greater the area under the curve for measured fluorescence of DCFH oxidized into DCF by ROSs as a function of time, the less the material is capable of quickly neutralizing the primary ROSs generated from the standardized initial photochemical reaction. The TAS is thus greater when the area under the curve is smaller.

Figure 1:
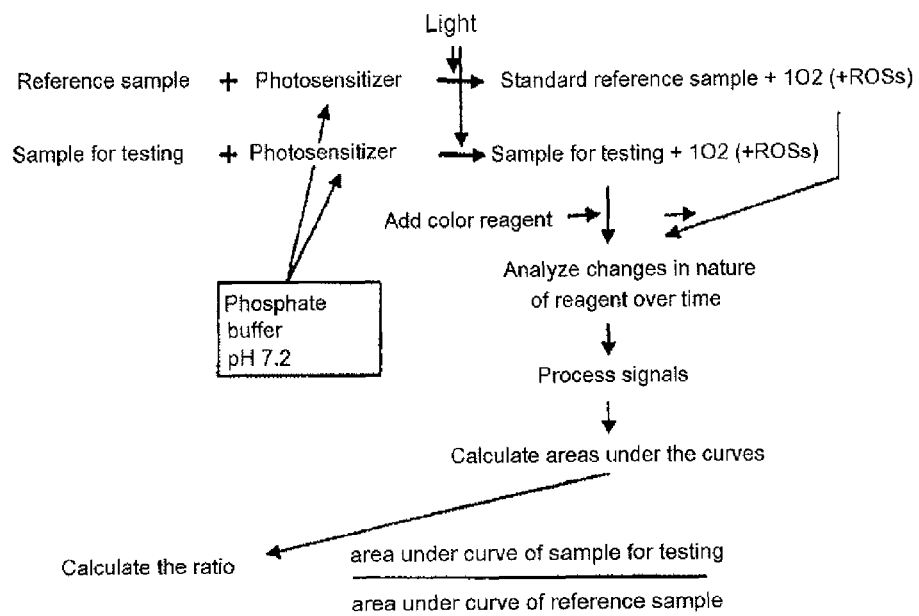
FIG. 1 is a general schematic view of the method of the invention in a version for measuring the total antioxidant status (TAS) of a biological material or medium.
Figure 2:
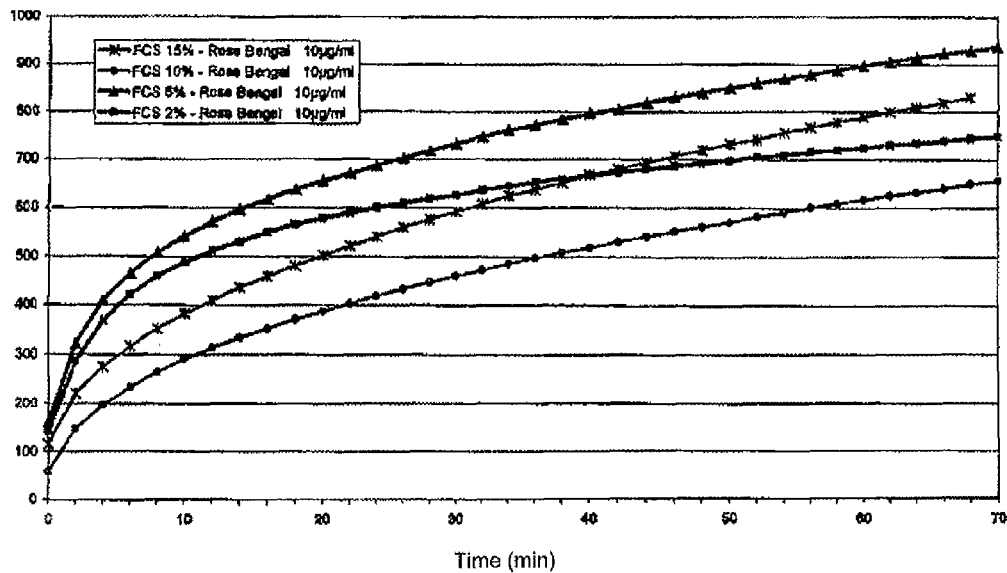
FIG. 2 shows the variation in the fluorescence signal from dichlorofluoresceine (DCF) expressed in arbitrary units as a function of time, and the concentration of fetal calf serum (FCS) in the sample for testing after irradiation at 10 joules per square centimeter ($J/cm^2$) in the presence of rose bengal at a concentration of 10 milligrams per milliliter (mg/mL)

An example of such curves is given in FIG. 2. Each curve corresponds to a serum concentration of the sample for testing. Thus, the samples present serum concentrations of 2%, 5%, 10%, or 15%.

The solution in which the photosensitive agent enabling primary ROSs to be produced is subjected to light irradiation and in which the ROSs are subsequently detected by the DCFH-DCF system as described above has a pH that is buffered to a pH of 7.2 by a highly concentrated phosphate buffer (250 mM). This condition enables a good fluorescence signal to be obtained, eliminates artifacts associated with variations in pH as a result of adding solutes or compounds, and is compatible with biological pH.

In an application for measuring the antioxidant status of a serum in order to detect an anomaly in said antioxidant status associated with a disease, the ROSs are produced directly in the serum of the patient for testing and compared with the values obtained in a reference serum and with normal values previously obtained in a healthy control sample.

Under such circumstances, the method includes at least one step of subjecting at least a first reference mixture to the same photochemical and colorimetric reactions as the sample for testing. This first mixture is formed by mixing a photosensitive agent and serum from a panel of healthy controls. The method also includes subjecting said reference mixture and the mixture for testing forming a second control to the same colorimetric reaction as the mixture for testing without any prior photochemical reaction. The results obtained enable results to be corrected.

In a clinical perspective, a blood sample may be taken prior to treatment, immediately after treatment, and then after a greater length of time. The results obtained after treatment are compared with the values before treatment. Thus, and by way of example, it is possible to verify the impact of extracorporeal circulation on the post-operative complication rate or to measure the impact of radiotherapy on a given patient.

The succession of steps measuring the influence of a biological tissue or a biological liquid in the disappearance of ROSs is reproduced for varying concentrations of the biological tissue or biological liquid for testing, and possibly containing substances for which it is desired to measure the antioxidant potential. Thus, the areas under the curve plotting variation in the fluorescence induced by the ROSs produced within the mixture change as a function of the modification in the antioxidant power induced by said materials, biological tissue, or biological liquid. When the antioxidant power increases, the curve is shifted downwards. When the antioxidant power decreases, it is shifted upwards. By measuring the slope of the curve, it is thus possible to characterize very accurately the TAS and thus to make subsequent comparisons possible, e.g. with other materials in which it is desired to measure TAS.

Figure 5:
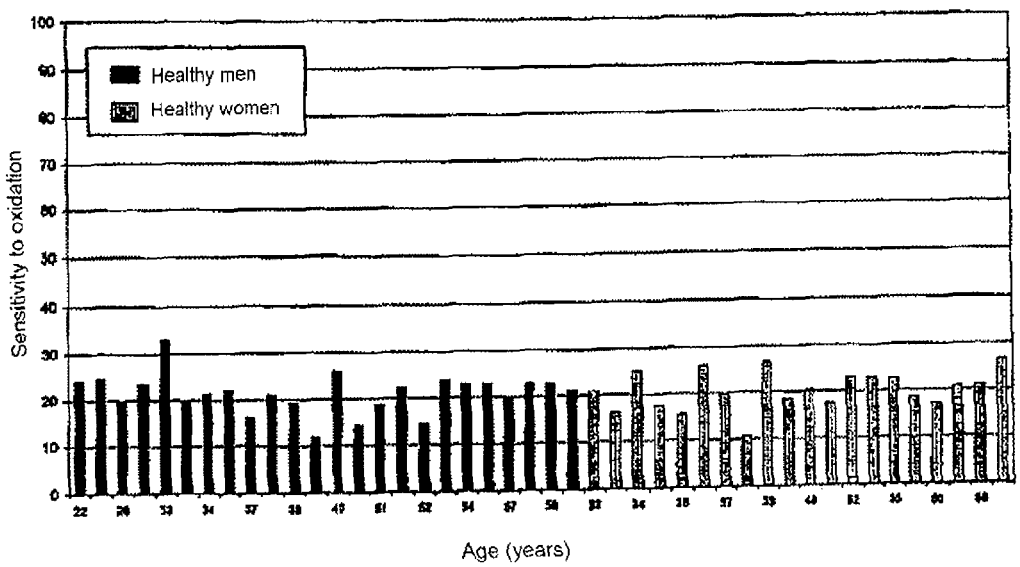
FIG. 5 shows the area under the curve of the dichlorofluoresceine (DCF) fluorescence signal as a function of age and sex for serum taken from 24 men and 20 women presumed to be healthy and subjected to light irradiation in the presence of rose bengal.

FIG. 2 shows the results obtained from a mixture of a sample for testing plus a photosensitive agent at different concentrations, with a control formed by the sample alone constituting a reference. The results are presented as a percentage of the reference control value. The areas under the curve are calculated for the sample for testing and for the reference sample. Tests performed using the method of the invention as described above make it possible to measure the antioxidant status of healthy human serums (FIG. 5). It has been possible to show that this potential is different for man and for woman for which it has been possible to calculate two mean values. Used in the same manner on pathological serums obtained from patients suffering from diabetes complicated by ischemia, a test value higher than the healthy control values was measured (FIG. 6) in patients suffering from unstable or complicated diabetes. Similar observations have been made in the field of cancerology with progressing cancers.

Finally, antioxidant potential has been analyzed on serums obtained from animals of different species. We have observed both significant variation between the species and also significant variation between individuals within a given species, giving rise to a standard deviation that is large, but nevertheless smaller than with human serums (FIG. 7).

The curve shows the analysis of variation in the fluorescence of DCFH as it transforms into DCF as a function of time in the different solutions.

Depending on the type of ROS relative to which the status of a material, biological tissue, or biological liquid is measured, it is possible to select a photosensitive agent that is suitable for preferentially producing such and such a type of ROS. Nevertheless, it is preferable to select a photosensitive agent that produces a majority of the most highly energetic species, i.e. $^1O_2$. Thus, an example of a photostabilizer suitable for use could be rose bengal, and another could be tetra (4 sulfonato-phenyl)porphyrin (TPPS), both of which have quantum efficiencies of 0.75 in producing $^1O_2$. Another criterion for selection is the absence of a chemical reaction between the photostabilizer and the sample for testing when the mixture is sheltered from light. The light irradiation should be performed at the absorption maximum of the spectrum of the photosensitizer, i.e. at 520 nm for rose bengal in the context of a preferred example. The energy delivered to the mixture of sample and photosensitizer is 10 $J/cm^2$ in a preferred application. Light irradiation and subsequent detection of fluorescence must be performed under strict thermostatic conditions.

Figure 4:
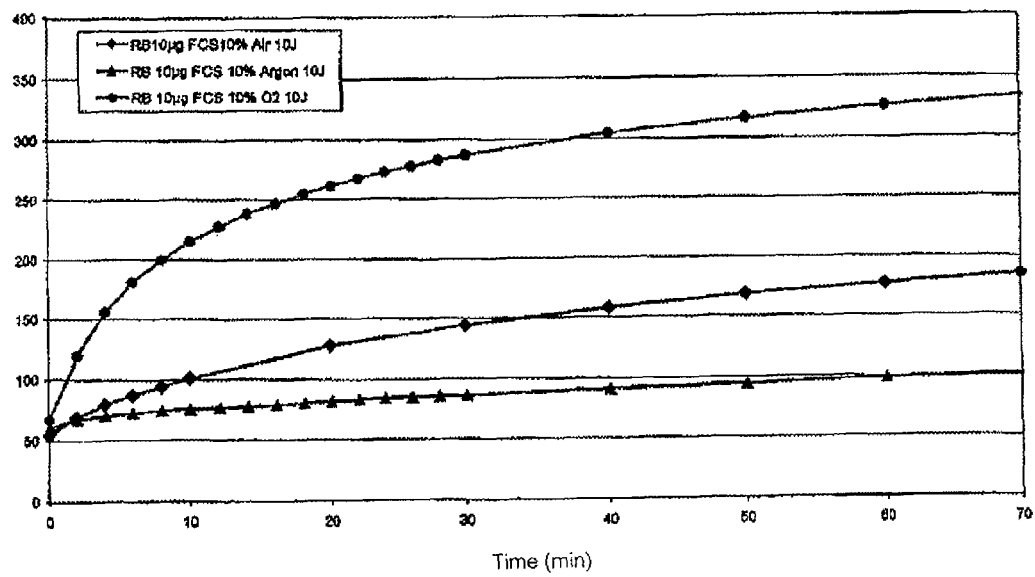
FIG. 4 shows the variation in the fluorescence of the dichlorofluoresceine (DCF) signal expressed in arbitrary units as a function of time in a medium containing the serum and previously subjected to light irradiation in the presence of rose bengal in a normal atmosphere or an atmosphere that is saturated in argon or in nitrogen.

FIG. 4 shows that the initial photochemical reaction does indeed give rise to the production of ROSs, and in particular of $^1O_2$, since this reaction can be partially inhibited when irradiating in an atmosphere that is saturated with $N_2$, or even more clearly in an atmosphere that is saturated with argon (FIG. 6).

Various tests exist that make it possible to evaluate the antioxidant power of biological materials. Amongst these methods, the reference method is known as "Randox". The method of the invention differs significantly from that test insofar as it uses an optical method for producing ROSs (thereby limiting artifacts associated with the potential introduction of contaminants, e.g. heavy metals, or iatrogenic reactions). Furthermore, the use of singlet oxygen $^1O_2$ for such a reaction (lifetime extremely short, minimum consumption of oxygen in the medium and hence minimized risk of artifacts), having maximum oxidizing power, enables total overall detection of the induced ROSs. Furthermore, since the duration of the irradiation is very short, and in any event always terminated when adding the reagent for detecting the induced ROSs immediately after the end of light irradiation, the reactivity of the DCF reagent relative to light matters little and the reagent measures only captured ROSs. This also leads to an absence of artifacts. Furthermore, the fluorescence obtained after a Randox reaction is very unstable with the signal dropping by 50% in 60 seconds following the measurement time, with the optimum time recommended by the supplier being about 3 minutes, thus making it impossible to perform any analysis of the way ROSs disappear as a function of time.

The method of the invention may be implemented in particular in an installation that is in the form of an integrated assembly, preferably a portable assembly, comprising at least an enclosure, which is preferably thermostated, means for applying light irradiation in said enclosure, means for measuring the intensity of a light signal within said enclosure, and means for acquiring and processing data from the measurement means. The term "integrated assembly" is used to mean an installation including all of the above-described elements and forming a one-piece assembly. The means for providing light irradiation in the enclosure may be constituted by a simple diode. The means for measuring the intensity of a light signal may be constituted by a strip of diodes or photomultipliers. The enclosure may define at least two compartments, one of the compartments serving to receive the photosensitive agent, the other serving to receive the agent that is suitable for forming a chromogen or fluorescent substance. Said compartments are suitable for communicating with each other, either by pouring the content of one of the compartments into the other, or by breaking a connection zone between the compartments so as to enable the colorimetric reaction to take place after irradiation. A third compartment may be provided for receiving the sample for testing and for measuring its absorbance. By means of such an installation, the operator need merely insert the sample into the thermostated enclosure. The means for acquiring and/or processing the data from the measurement means may likewise be simplified and may be implemented essentially in the form of computer processing.

The method may also be implemented with the help of a test kit that comprises at least firstly a support defining at least two compartments and secondly a photosensitive agent and an agent suitable for forming the chromogen or fluorescent substance, each in a buffered medium in one of the compartments of the support, said compartments being suitable for being put into communication with each other. Once more, the compartments may be moved relative to each other in order to enable the content of one of them to be poured into the content of the other. The compartments may also be provided with a removable or destroyable separation zone that makes it possible, after applying the light irradiation, to put the contents of said compartments into communication with each other. The kit is for use by operators who already have available: irradiation means; means for measuring the intensity of a light signal; and means for acquiring and/or processing data from the measurement means.

The invention claimed is:

1. A method of measuring the total antioxidant status (TAS) of a biological sample obtained from a human or animal organism to determine said organism's ability to withstand reactive oxygen species (ROSs), comprising the following steps:
   a) putting the biological sample for testing into contact with a photosensitive agent in a liquid medium to form a mixture for testing;
   b) subjecting said mixture for testing to a dose of light irradiation at a wavelength that is absorbed by the photosensitive agent in order to give rise, by a photochemical reaction at least between the light and the photosensitive agent, to at least the production of singlet oxygen suitable for co-operating with said sample to form ROSs;

c) adding, after irradiation, a compound that reacts colorimetrically in the presence of ROSs to form a chromogen or fluorescent substance;

d) measuring the quantity of chromogen or fluorescent substance produced over time in order to determine the ability of said sample to withstand ROSs by inhibiting them, a low level of chromogen or fluorescent substance production corresponding to said sample having a high ability to withstand ROSs;

e) subjecting at least one reference mixture formed by putting a reference biological sample from a presumed healthy organism in contact with a photosensitive agent to a dose of light irradiation at a wavelength that is absorbed by the photosensitive agent to form ROSs, adding a compound that reacts colorimetrically in the presence of ROSs to form a chromogen or fluorescent substance, and measuring the quantity of chromogen or fluorescent substance produced over time as carried out for the mixture for testing; and f) comparing the measured quantity of chromogen or fluorescent substance obtained from the mixture for testing with the measured quantity of chromogen or fluorescent substance obtained from said at least one reference mixture to obtain the TAS of the biological sample of said organism and determine said organism's ability to withstand ROSs.

2. The method according to claim 1, further comprising:

during measuring step d), measuring over time, for each mixture, the quantity of chromogen or fluorescent substance produced as an intensity of the light or fluorescent signal from said substance; and during comparing step e), processing said intensity of the light or fluorescent signal measurements, for each mixture, by establishing a curve for the intensity of the light signal from the chromogen or fluorescent substance as a function of time, and then calculating the area under the curve, wherein said comparing of measured quantities is performed by determining the ratio between the areas of the mixture for testing and of the at least one reference mixture.

3. The method according to claim 1, wherein absorbances of said biological sample for testing and of the reference biological sample are measured prior to putting the biological sample for testing and the reference biological sample into contact with the photosensitive agent.

4. The method according to claim 1, wherein the photosensitive agent produces a majority of singlet oxygen $^1O_2$, and said agent is one of rose bengal and tetra (4 sulfonato-phenyl) porphyrin (TPPS).

5. The method according to claim 1, wherein the photosensitive agent does not react with the biological sample for testing in the absence of light, and said photosensitive agent is irradiated at a selected wavelength corresponding to the spectrum absorption maximum of the photosensitive agent.

6. The method according to claim 1, wherein the compound that reacts to form a chromogen substance is the reduced dichlorofluoresceine-dichlorofluoresceine system (DCFH-DCF).

7. The method according to claim 1, wherein the photochemical and colorimetric reactions are performed at a pH that is neutral or close to biological pH in a thermostated enclosure.

8. The method according to claim 1, wherein the biological sample for testing from a human or animal organism is a biological fluid selected from the group consisting of serum, plasma, and a tissue extract in solution.

9. The method according to claim 1, wherein for each mixture, the quantity of chromogen or fluorescent substance produced is measured as an intensity of the light or fluorescent signal from said sample over a period of time of not less than 45 min.

10. The method according to claim 2, wherein absorbances of said biological sample for testing and of the reference biological sample are measured prior to putting the biological sample for testing and the reference biological sample into contact with the photosensitive agent in order to receive light irradiation, the absorbances of said sample for testing and of the reference sample are measured.

* * * * *